United States Patent
Eifler (10) Patent No.: US 12,268,814 B2
(45) Date of Patent: Apr. 8, 2025

(54) DEVICE FOR SUPPORTING A RESPIRATORY MASK WITH INTEGRAL FUNCTIONAL ELEMENTS

(71) Applicant: Loewenstein Medical Technology S.A., Luxembourg (LU)

(72) Inventor: Martin Eifler, Glueckstadt (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1036 days.

(21) Appl. No.: 16/691,699

(22) Filed: Nov. 22, 2019

(65) Prior Publication Data

US 2020/0179634 A1 Jun. 11, 2020

(30) Foreign Application Priority Data

Nov. 30, 2018 (DE) .......................... 102018130438.2

(51) Int. Cl.
*A61M 16/06* (2006.01)

(52) U.S. Cl.
CPC ...... *A61M 16/065* (2014.02); *A61M 16/0683* (2013.01)

(58) Field of Classification Search
CPC ........... A61M 16/06–0694; A61M 2016/0661; A62B 18/02; A62B 18/025; A62B 23/02; A62B 23/025
See application file for complete search history.

(56) References Cited

U.S. PATENT DOCUMENTS

| | | | |
|---|---|---|---|
| 6,119,693 A | 9/2000 | Kwok | |
| 6,532,961 B1* | 3/2003 | Kwok | A61M 16/06 128/206.21 |
| 6,823,869 B2* | 11/2004 | Raje | A61M 16/0683 128/206.24 |
| 8,353,294 B2* | 1/2013 | Frater | A61M 16/0611 128/207.11 |
| 8,967,148 B2* | 3/2015 | Eifler | A61M 16/0638 128/206.28 |
| 2004/0182398 A1* | 9/2004 | Sprinkle | A61M 16/0622 128/207.13 |
| 2005/0072428 A1* | 4/2005 | Ho | A61M 16/06 128/205.25 |
| 2006/0144399 A1* | 7/2006 | Davidowski | A61M 16/0057 128/205.12 |
| 2008/0135050 A1* | 6/2008 | Hitchcock | A61M 16/0683 128/207.11 |

(Continued)

FOREIGN PATENT DOCUMENTS

EP 1205205 A2 5/2002

OTHER PUBLICATIONS merriam-webster.com, https://www.merriam-webster.com/dictionary/base (last visited Aug. 15, 2024).*

(Continued)

*Primary Examiner* — Valerie L Woodward
(74) *Attorney, Agent, or Firm* — Abel Schillinger, LLP (57) ABSTRACT

A forehead support for supporting a respiratory mask having a forehead support stem and a forehead rest. The forehead rest comprises a guide bar which can be guided over a resilient element that is formed in the forehead support stem. The forehead support stem may be forked.

16 Claims, 12 Drawing Sheets

(56) References Cited

U.S. PATENT DOCUMENTS

| | | | | |
|---|---|---|---|---|
| 2008/0168991 A1* | 7/2008 | Eifler | ............... | A61M 16/06 |
| | | | | 128/205.25 |
| 2010/0000542 A1* | 1/2010 | Chu | ............ | A61M 16/0655 |
| | | | | 128/206.21 |
| 2011/0094516 A1* | 4/2011 | Chang | ............... | A61M 16/06 |
| | | | | 128/206.28 |

OTHER PUBLICATIONS merriam-webster.com, www.merriam-webster.com/dictionary/stem); see Stem Definition (noun (1)) 1(b), merriam-webster.com, https://www.merriam-webster.com/dictionary/stem (last visited Aug. 15, 2024).*

* cited by examiner

DEVICE FOR SUPPORTING A RESPIRATORY MASK WITH INTEGRAL FUNCTIONAL ELEMENTS

CROSS-REFERENCE TO RELATED APPLICATIONS

The present application claims priority under 35 U.S.C. § 119 of German Patent Application No. 102018130438.2, filed Nov. 30, 2018, the entire disclosure of which is expressly incorporated by reference herein.

BACKGROUND OF THE INVENTION

1. Field of the Invention

The present invention relates to a forehead support for supporting a respiratory mask having a forehead support stem and a forehead rest, wherein the forehead rest comprises a guide bar which can be guided over a resilient element. The present invention relates further to a forehead support for supporting a respiratory mask having a forehead support stem and a forehead rest, wherein the forehead rest comprises a guide bar. The present invention relates further to a respiratory mask comprising in each case one of the forehead supports described above.

2. Discussion of Background Information

Such forehead supports are adjusting devices which serve to support a respiratory mask in the region of a patient's forehead in a manner which is adapted to the particular facial geometry of the patient. The known forehead supports have an adjustment facility either for carrying out an adjustment substantially perpendicularly to the forehead and thereby changing the effective distance between the forehead and the mask, or for carrying out an adjustment substantially parallel to the surface of the face and thereby making an adaptation to the particular forehead height. Mechanical adjusting mechanisms or the purposive incorporation of elements with mutually different, suitable sizing are known for this purpose.

A forehead support having an adjusting device for defining an effective distance between the forehead and the mask is described, for example, in U.S. Pat. No. 6,119,693, the entire disclosure of which is incorporated by reference herein. There is disclosed therein a bridge-like forehead support which is connected to the respiratory mask via two carrying arms. A transverse carrier of the support element, which carries two forehead cushions, has latching devices in the region of its extent facing the supporting arms. By locking the supporting arms in different latching devices, a different distance between the transverse carrier and the respiratory mask and thus a different effective distance between the forehead and the mask is defined.

Moreover, there is known from EP 1 205 A2, the entire disclosure of which is incorporated by reference herein, a device for supporting a respiratory mask in the region of a patient's forehead, comprising at least one supporting element arranged in the region of at least one retaining arm of the respiratory mask and connected by an adjusting device to the retaining arm, wherein the adjusting device comprises a longitudinal guide in the direction of a longitudinal axis of the retaining arm and a transverse guide for positioning the supporting element substantially transversely to the longitudinal axis.

The devices known hitherto are not yet able to meet all the requirements in terms of their ease of adjustment and their usability which result from a use by the patient himself.

In view of the above situation, it would be advantageous to have available a device of the type mentioned in the introduction which provides versatile adjustability while at the same time being simple to operate.

SUMMARY OF THE INVENTION

The present invention provides a forehead support and a respiratory mask according to the independent claims. Further developments and advantageous embodiments are subject-matter of the dependent claims. Further advantages and features will become apparent from the general description and the description of the exemplary embodiments.

The present invention provides a forehead support for supporting a respiratory mask having a forehead support stem and a forehead rest, wherein the forehead rest comprises a guide bar which can be guided over a resilient element.

The present invention also provides a forehead support for supporting a respiratory mask having a forehead support stem and a forehead rest, wherein the forehead rest comprises a guide bar which is connected to the forehead support stem, wherein the guide bar comprises a resilient element.

The resilient element is in the form of a spring or in the form of a resilient portion which can be produced by the injection molding process, which forms a movable connection between the guide bar and the forehead rest.

The guide bar can be movably and lockably arranged in the forehead support stem.

The guide bar can also be unmovable and in one piece with the forehead support stem.

Subject matter of the present invention also is a forehead support for supporting a respiratory mask having a forehead support stem and a forehead rest, wherein the forehead rest comprises a guide bar which is connected to the forehead support stem, wherein the guide bar comprises a resilient element, wherein the resilient element forms the connection between the forehead rest and the guide bar, wherein the guide bar is unmovable and/or in one piece with the forehead support stem.

Subject matter of the present invention also is a forehead support for supporting a respiratory mask having a forehead support stem and a forehead rest, wherein the forehead rest comprises a guide bar which can be guided over a resilient element, wherein the resilient element is formed in the forehead support stem and the guide bar is movably and lockably arranged in the forehead support stem.

According to the invention, the resilient element is integrally formed in the forehead support stem. The resilient element integrated into the forehead support stem offers the advantage that a one-piece forehead support stem can be formed. On the one hand this simplifies operation of the forehead support, and on the other hand the forehead support is thus easier to clean. A further aspect is the aesthetics, a slim, one-piece forehead support is perceived by a user to be more pleasing, which contributes toward improved therapy by acceptance.

In an embodiment, the resilient element is in the form of a spring. The spring force of the spring is generally between 2 N and 50 N, in particular between 10 N and 30 N. The spring is usually S-shaped. Alternatively, the spring can be U-shaped. Typically, an upper folded region of the spring is formed close to the patient and a lower folded region is arranged remote from the patient. By designing the upper region of the spring to be close to the patient, the guide bar can more easily be inserted into the forehead rest. The design and arrangement of the spring thus contributes toward simplified assembly. Alternatively, the spring can have a reverse fold, with a fold close to the patient in the upper region of the spring and a fold close to the patient in the lower region of the spring.

In an embodiment, the forehead support stem is forked with a first stem portion and a second stem portion, wherein the resilient element is formed between the first stem portion and the second stem portion. Forked here means that the first stem portion and the second stem portion have a common base, starting from which the first stem portion and the second stem portion extend in a V-shape or U-shape. The first stem portion and the second stem portion form the receiving region for the integrally arranged resilient element, which can be in the form of an integrally arranged spring.

Usually, the first stem portion and the second stem portion each have a guide projection. A guide projection thereby extends starting from the end of a respective stem portion that is remote from the fork base at an angle of between 45° and 100°, in particular between 85° and 95°, in the direction toward the respective other stem portion of the forked forehead support.

In a further embodiment, the first stem portion and/or the second stem portion comprise at least one locking pin. The locking pin can be triangular or square as well as round or oval. The locking pin can thus have any desired geometric shape. The locking pin is generally arranged on the respective guide projection of the respective stem portion. Alternatively, the at least one locking pin is arranged directly on the respective stem portion.

In a further development of the invention, the first stem portion and/or the second stem portion comprises at least one guide projection, wherein at least one locking pin is formed on the at least one guide projection. The guide projection is configured as a prolongation, in order to position the locking pin of the respective stem portion in the region of the guide bar.

In an embodiment, the guide bar lies on the resilient element, wherein the resilient element supports and limits the guide bar. The guide bar is usually U-shaped or V-shaped. Alternatively, the guide bar is in the form of a straight rod. The guide bar is usually arranged centrally between the first stem portion and the second stem portion of the forehead support stem without being in contact with the first stem portion and the second stem portion, wherein the guide bar is usually arranged lying on the resilient element. A respective guide projection is further adapted to guide the guide bar. The arrangement of the guide bar on the integrally formed resilient element offers the advantage that the guide bar is movable both horizontally and vertically. As a result of the horizontal and vertical movability of the forehead rest, the forehead rest is particularly flexible.

In a further embodiment, the first stem portion and the second stem portion each comprise at least one bearing surface for supporting the resilient element. The respective bearing surface is configured as a narrow projection. The bearing surface is usually rectangular. Alternatively, the bearing surface is semicircular. The resilient element is usually supported in each case on a bearing surface of a respective stem portion.

In a further development, the first stem portion and the second stem portion are configured and formed as an operating element. By pressing the first stem portion and the second stem portion together, the forehead support is operated/adjusted. The guide bar of the forehead support, and thus the position of the forehead rest, can thereby be adjusted with one hand. In general, the forehead support according to the invention is configured as a guiding, locking, operating element.

In an embodiment, the resilient element comprises at least one limiting projection which is adapted to limit the guiding of the guide bar. The limiting projection is arranged on a surface of the resilient element that faces toward the guide projections. In general, the limiting projection is semicircular. Alternatively, the limiting projection is angular or oval. The limiting projection is adapted to engage into a running surface which is formed in a running region on an underside of the guide bar. The limiting projection is adapted to limit the guiding of the guide bar at the end of the running surface. Optionally, the forehead support comprises at least two limiting projections.

In a further embodiment, the guide bar has recesses. In general, the recesses are formed in the region of the inner surface of the U-shaped guide bar. Alternatively, the recesses are formed on an outer surface of the guide bar. The recesses are adapted to receive at least one locking pin. Typically, the recesses are angular. Alternatively, the recesses can be semicircular or oval. The recesses can alternatively have any geometric shape. In general, each side of the U-shaped guide bar has at least two recesses.

In an embodiment, the locking pins are adapted to engage into the recesses of the guide bar, to limit the guide bar laterally, and to center the guide bar on the resilient element. Advantageously, the locking pins have a shape corresponding to the shape of the recesses which receive the locking pins. The locking pins are adapted to come out of the recesses when the first stem portion and the second stem portion of the forehead support stem are pressed together. When the forehead support stem is in the closed state, the locking pins thus do not reach into the recesses. In this state, the guide bar, which lies on the resilient element/spring, is movable. When the desired adjustment position has been reached, it is possible by releasing the pressed-together forehead support to guide the locking pins, for locking, back into recesses which, corresponding to the new position, are available for receiving locking pins.

In an embodiment, the forehead rest is movably connected to the guide bar. This offers the advantage that an angle between the forehead rest and the guide bar is flexible. This offers better adaptation possibilities when adapting the forehead support, in particular the forehead rest of the forehead support, to the patient's head. This contributes to a greater feeling of comfort for the patient. Movable can thereby mean that the forehead rest is connected to the guide bar via a joint or a flexible material.

In a further embodiment of the invention, the forehead rest is flexibly adjustable, wherein relative to the longitudinal axis of the guide bar a tilting movement of the forehead rest is adjustable in an angle between 1° and 30°. In general, the forehead rest can thus be adapted to an inclination of the patient's forehead. The flexible adjustability of the forehead rest contributes to greater accuracy of fit of the forehead support and thus to improved sealing of a respiratory mask relative to the patient's head.

In an embodiment of the invention, a connection between the forehead rest and the guide bar is formed of a resilient material. A resilient material is generally a silicone, a TPE or another plastics material. Forming the connection by means of a resilient material offers the advantage that the connection has the same flexible properties in every direction.

In an alternative embodiment, the connection between the forehead rest and the guide bar is a ball joint or a pivot joint. Forming the connection as a ball joint or pivot joint offers the advantage of a fixed mechanical connection of the forehead rest with the guide bar.

In a further development of the invention, the resilient element comprises a groove which is adapted to guide the resilient element in the guide bar. This is advantageous in particular when the resilient element is in the form of a spring, since the spring can be guided precisely along the guide bar by the groove.

The present invention relates further to a forehead support for supporting a respiratory mask having a forehead support stem and a forehead rest, wherein the forehead rest comprises a guide bar.

According to the invention, the forehead support stem is forked with a first stem portion and a second stem portion. Forked means that the first stem portion and the second stem portion have a common base, starting from which the first stem portion and the second stem portion extend in a V-shape or U-shape.

In a further form, the forehead support stem is adapted to receive a resilient element. The first stem portion and the second stem portion thereby form the receiving region for the resilient element, which can be in the form of an integrally arranged spring.

The present invention further comprises a respiratory mask comprising a forehead support for supporting a respiratory mask having a forehead support stem and a forehead rest, wherein the forehead rest comprises a guide bar which can be guided over a resilient element, according to one of the features described hereinbefore. Such a respiratory mask offers the advantage that the respiratory mask, in terms of its ease of adjustment and usability, is able to meet the requirements which result from a use by the patient himself.

The present invention further comprises a respiratory mask comprising a forehead support for supporting a respiratory mask having a forehead support stem and a forehead rest, wherein the forehead rest comprises a guide bar, according to one of the features described hereinbefore.

BRIEF DESCRIPTION OF THE DRAWINGS

Preferred exemplary embodiments of the invention will be explained hereinbelow by means of highly simplified schematic representations, in which.

In the figures, the same structural elements have the same reference numerals.

DETAILED DESCRIPTION OF EXEMPLARY EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
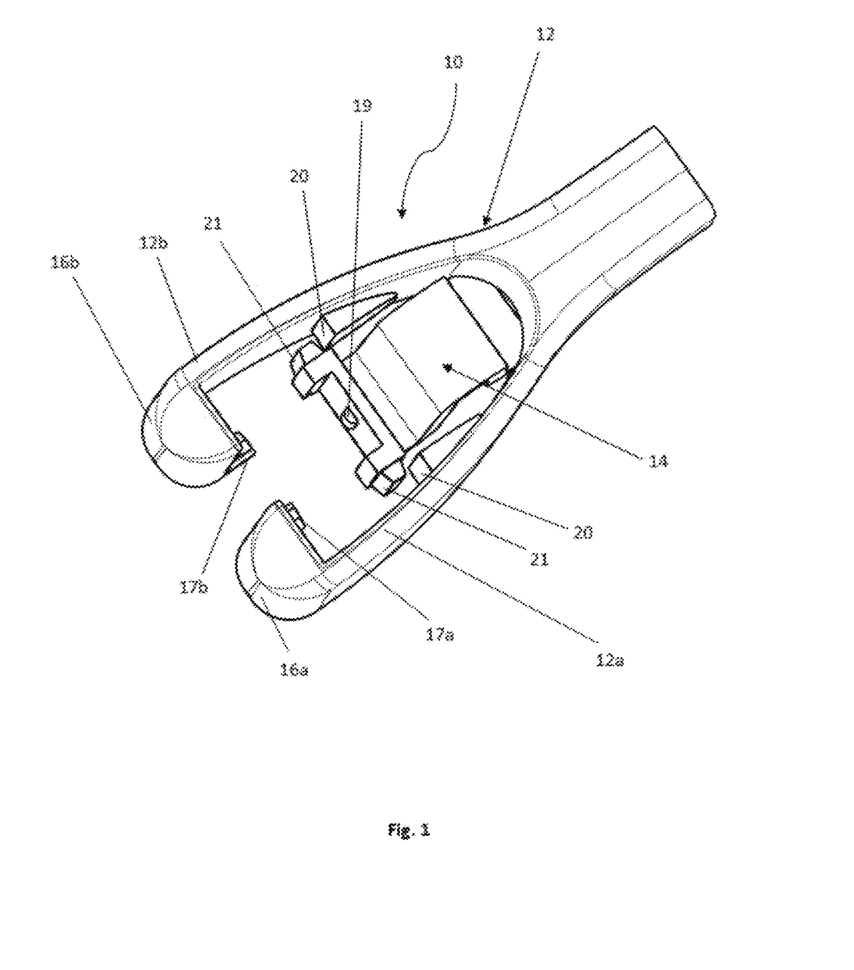
FIG. 1 shows a perspective representation of an embodiment of a forehead support having a resilient element integrated into a forehead support stem, wherein the resilient element is in the form of a spring.

FIG. 1 shows a perspective representation of an embodiment of a forehead support 10 having a resilient element 15 integrated into a forehead support stem 12 of the forehead support 10, wherein the resilient element 15 in the present embodiment is in the form of a spring 15.

An upper region of the forehead support 10 is shown. The forehead support stem 12 is forked and comprises a first forehead support portion 12a and a second forehead support portion 12b. The first forehead support portion 12a and the second forehead support portion 12b each have a guide projection 16a, 16b. On each of the guide projections 16a, 16b there is formed a locking pin 17a, 17b. Between the first forehead support portion 12a and the second forehead support portion 12b, the spring 15 is formed integrated into the forehead support stem 12. The spring 15 is S-shaped and comprises retaining elements 21 which lie on bearing surfaces 20 which are formed on the first forehead support portion 12a and on the second forehead support portion 12b. The spring 15 comprises a limiting projection 19.

The forked forehead support stem 12 is constructed as a guiding element, as an operating element and as a locking element. The forehead support stem 12 thus combines a plurality of functionalities in one device. The forehead support 10 configured as an operating element offers the advantage that, via the forehead support 10 constructed according to the invention, the forehead support can easily be operated/adjusted on a patient's face with one hand, both by the patient and by a carer. The forehead support 10 configured as a guiding element offers the advantage that the forehead support 10 autonomously realizes the guiding and movability of the guide bar 14 by means of the integrated spring 15 and thereby determines vertical movability of the forehead rest 13. The forehead support 10 configured as a locking element offers the advantage that the position of the guide bar 14 on the spring 15 set by the patient or carer is retained by the locking pins 17a, 17b. Horizontal and vertical movability is maintained owing to the guide bar 14 supported on the spring 15. The contributes to improving contact of the forehead rest 13 on the face and to an increased feeling of comfort for the patient.

Figure 2:
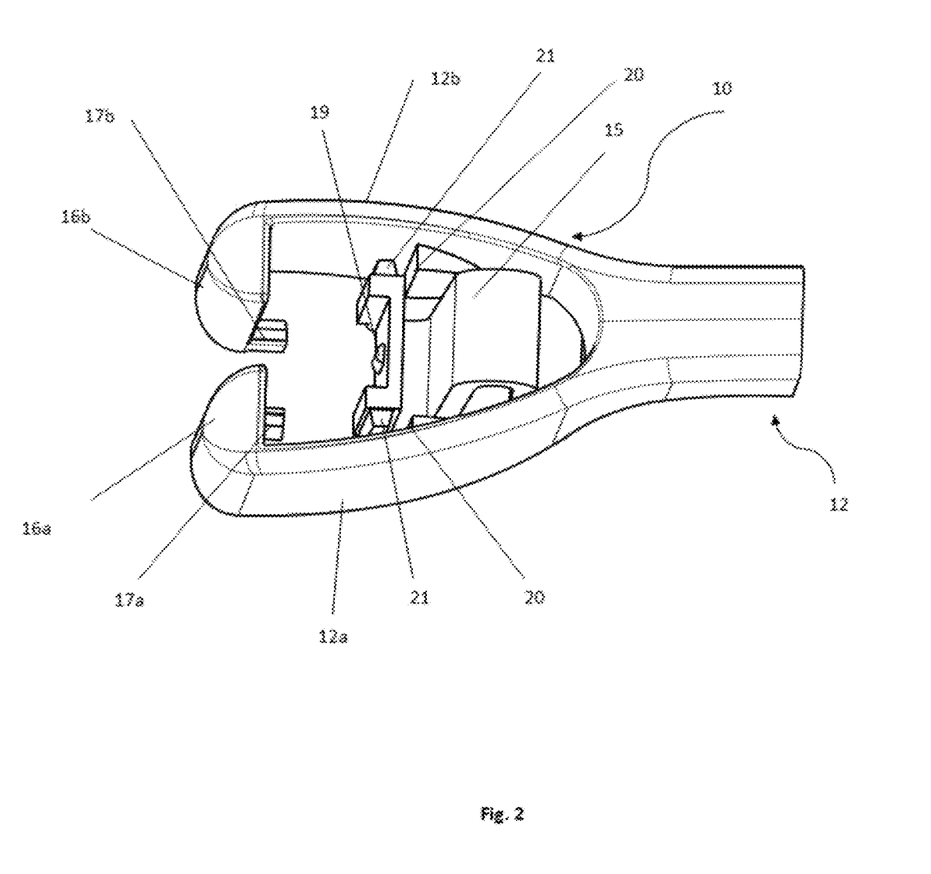
FIG. 2 shows a further perspective representation of the embodiment—shown in FIG. 1—of the forehead support with the spring integrated into the forehead support stem.

FIG. 2 shows a further perspective representation of the embodiment—shown in FIG. 1—of the forehead support 10 with the spring 15 integrated into the forehead support stem 12. In FIG. 2, the S-shaped form of the spring 15 can be seen, as can the integrated arrangement of the spring 15 in the forehead support stem 12. The spring 15 is mounted between the first stem portion 12a and the second stem portion 12b. In the embodiment of the spring 15 shown in FIG. 2, the spring 15 comprises at least three folds, wherein two folds point toward the patient and one fold points away from the patient. This embodiment of the spring 15 offers the advantage that, as a result of the double fold of the spring 15 toward the patient, greater stability of the forehead rest 13 and of the guide bar 14 is achieved.

Figure 3:
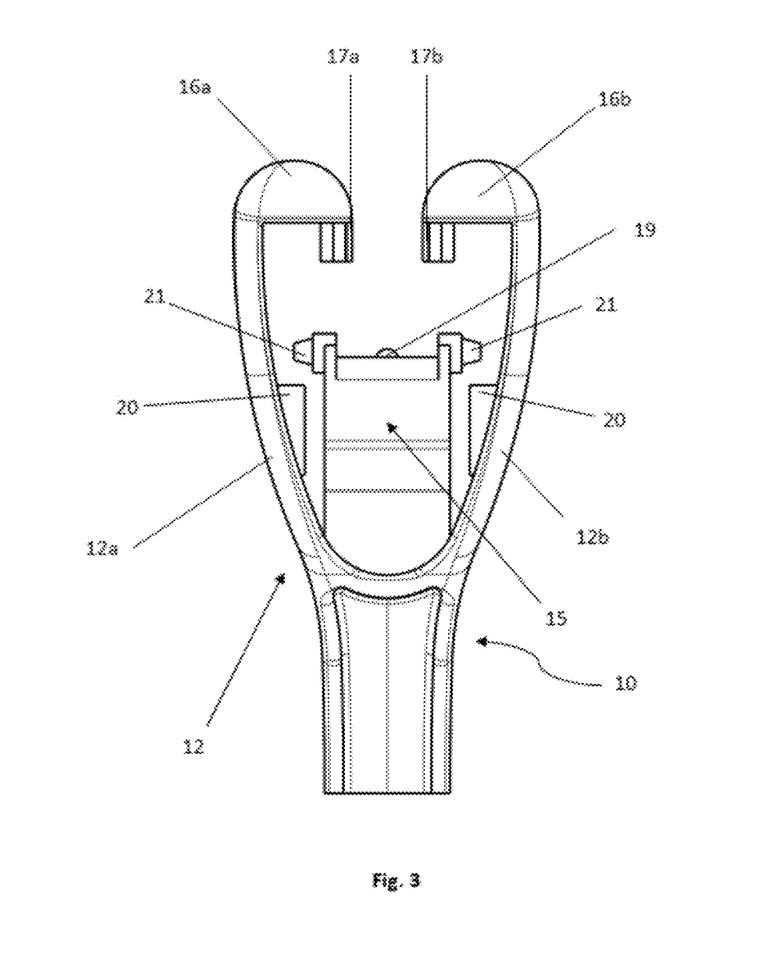
FIG. 3 is a front view of the embodiment—shown in FIG. 1 and FIG. 2—of the forehead support with the spring integrated into the forehead support stem.

FIG. 3 shows a front view of the embodiment—shown in FIGS. 1 and 2—of the forehead support 10 with the spring 15 integrated into the forehead support stem 12. In FIG. 3, the bearing surfaces 20, which are arranged on the first stem portion 12a and the second stem portion 12b, are shown. A limiting projection 19 is additionally shown. The limiting projection 19 is arranged on the spring 15. The limiting projection 19 is thereby arranged at the end of the spring 15 that faces away from the patient. The limiting projection 19 serves to limit the guiding of the guide bar 14. Thus, when the guide bar 14 is guided over the spring 15, the guide 14 can be guided only as far as the limiting projection 19. This offers the advantage that the guide bar 14 cannot easily be uncoupled from the spring 15 by the patient. The guide bar 14 can generally be guided over the limiting projection 19 only with increased force application. Thus, a patient cannot unintentionally detach the forehead rest 13 with the guide bar 14 from the respiratory mask 11.

Figure 4:
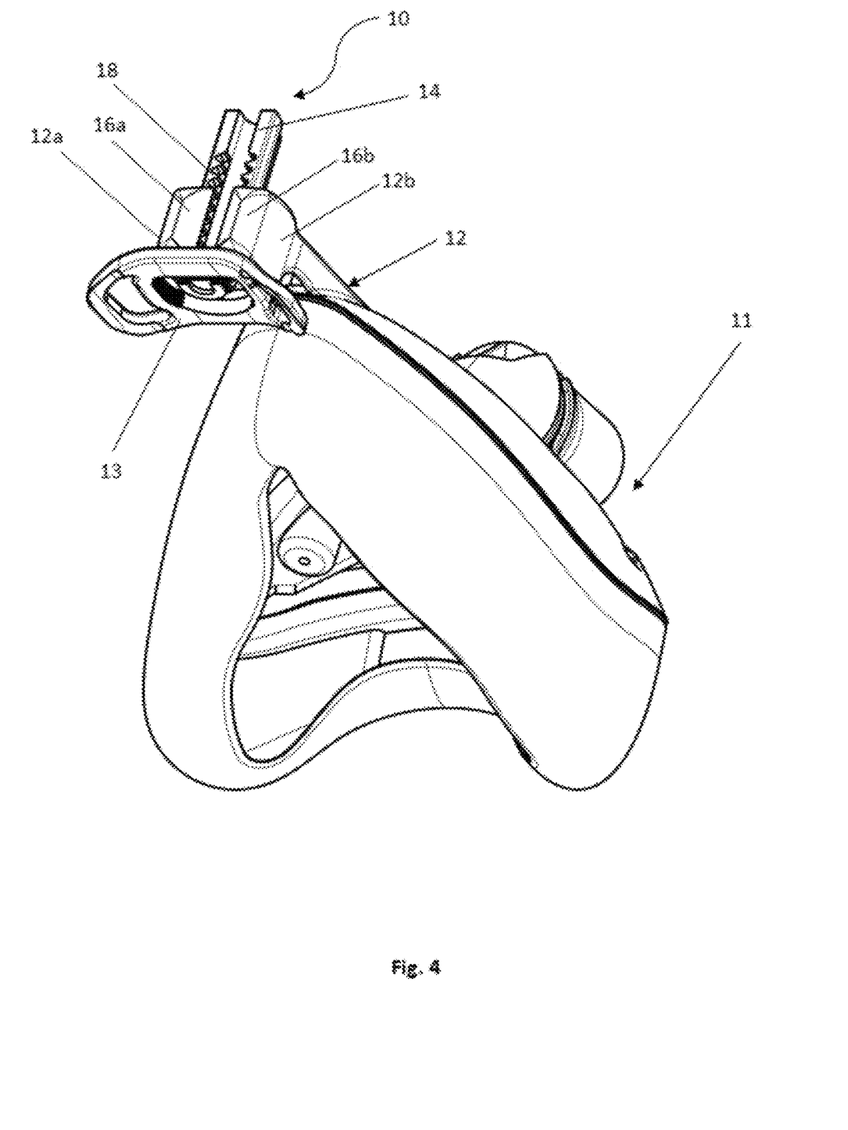
FIG. 4 shows a perspective representation of a respiratory mask comprising the forehead support—shown in FIGS. 1 to 3—with the spring integrated into the forehead support stem.

FIG. 4 shows a perspective representation of a respiratory mask comprising the forehead support 10—shown in FIGS. 1 to 4—with the spring 15 integrated into the forehead support stem 12. In FIG. 4, the forehead rest 13 is shown. In the present exemplary embodiment, the forehead rest 13 is in the form of a base plate which is adapted to lie against a patient's forehead. The base plate of the forehead rest 13 is adapted to receive a support cushion. The support cushion can be formed of a silicone or of a thermoplastic elastomer (TPE). Alternatively, the support cushion can be formed of a gel or a rigid plastics material.

Figure 5:
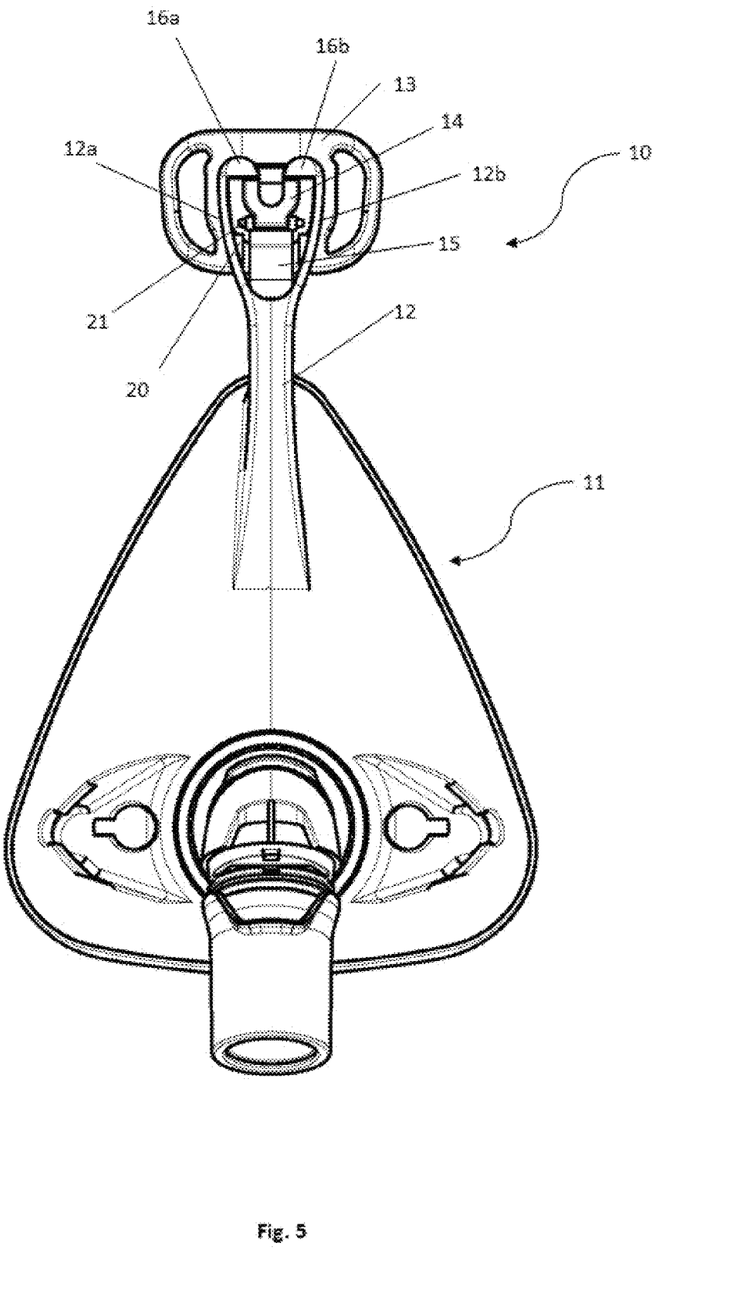
FIG. 5 is a front view of a respiratory mask comprising the forehead support—shown in FIGS. 1 to 4—with the spring integrated into the forehead support stem.

FIG. 5 shows a front view of a respiratory mask comprising the forehead support 10—shown in FIGS. 1 to 4—with the spring 15 integrated into the forehead support stem 12. The spring 15 is thereby arranged integrated between the first stem portion 12a and the second stem portion 12b. The first stem portion 12a and the second stem portion 12b each comprise a guide projection 16a, 16b. Also shown are the forehead rest 13, the guide bar 14, the bearing surfaces 20 and the retaining elements 21.

Figure 6:
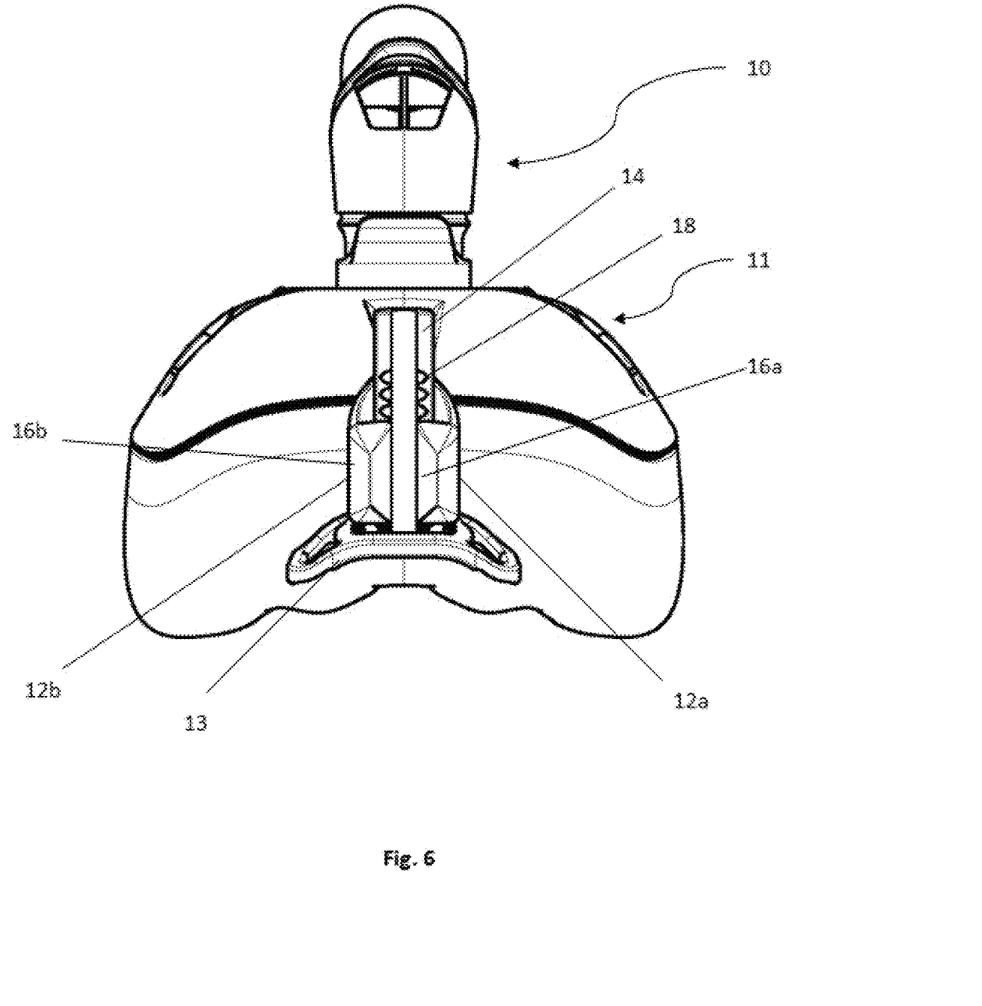
FIG. 6 is a top view of a respiratory mask 11 comprising a forehead support—shown in FIGS. 1 to 5.

FIG. 6 shows a top view of a respiratory mask 11 comprising a forehead support 10—shown in FIGS. 1 to 5. A top view of the guide bar 14 with the recesses 18, the first stem portion 12a, the second stem portion 12b, the guide projections 16a, 16b and the forehead rest 13 is shown.

Figure 7:
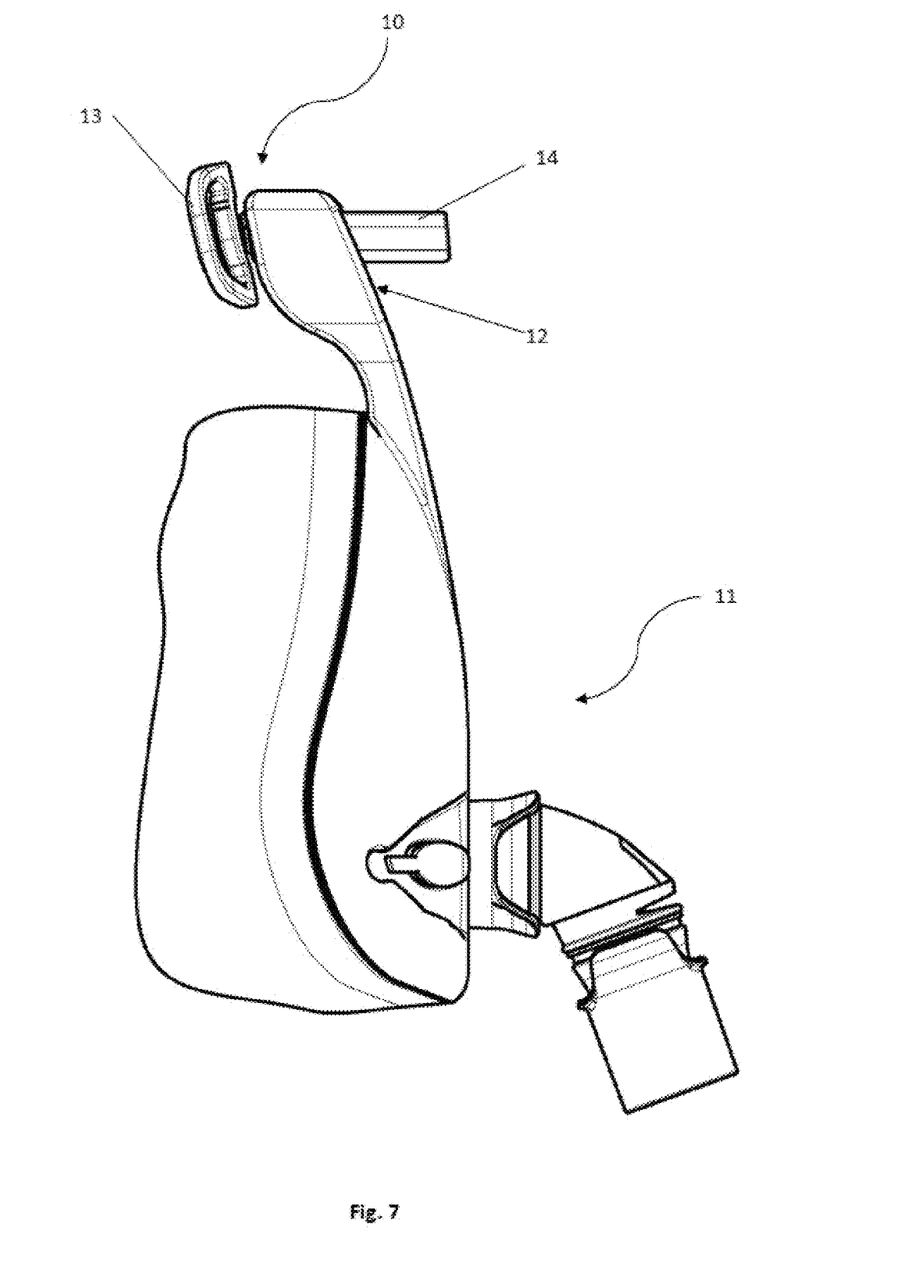
FIG. 7 is a side view of a respiratory mask comprising the forehead support—shown in FIGS. 1 to 6—with the spring integrated into the forehead support stem.

FIG. 7 shows a side view of a respiratory mask 11 comprising the forehead support 10—shown in FIGS. 1 to 6—with the spring 15 integrated into the forehead support stem 12. The arrangement of the forehead rest 13 and of the guide bar 14 in the forehead support 12 is shown.

Figure 8:
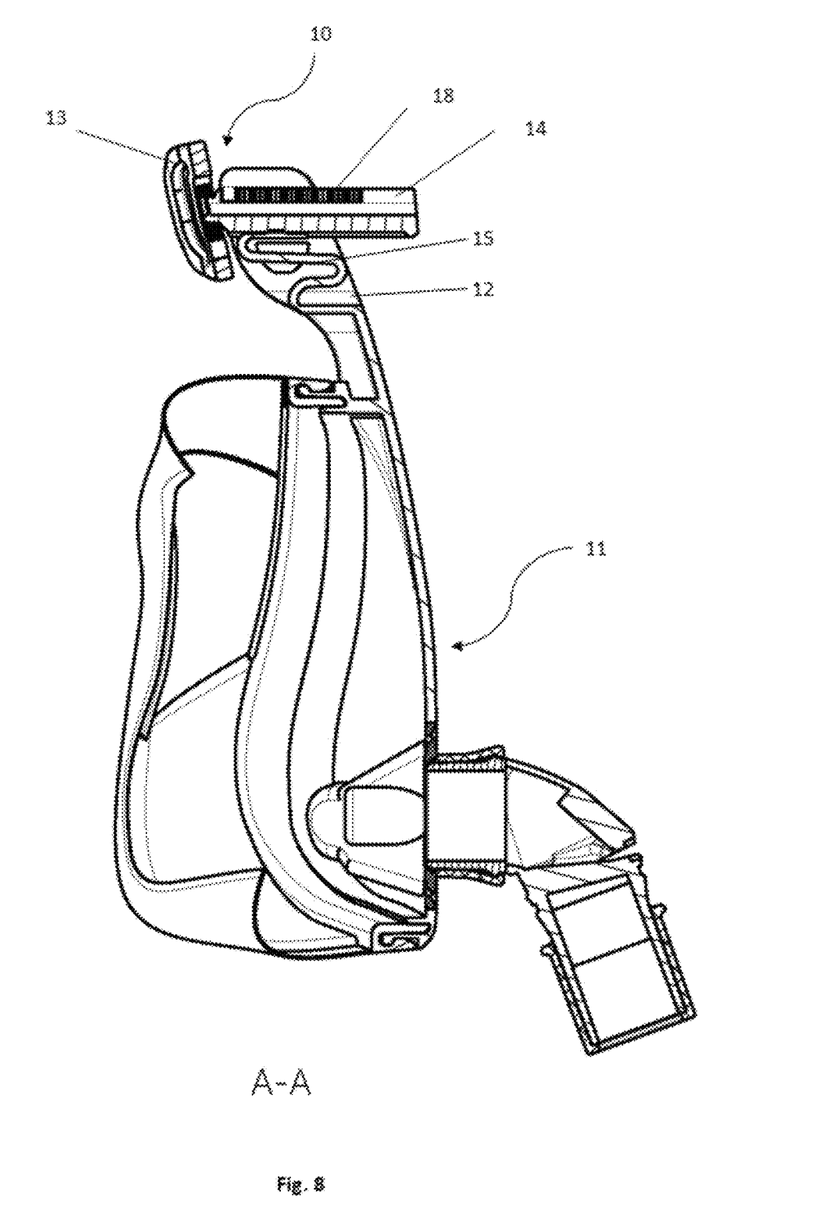
FIG. 8 is a vertical cross-section of a respiratory mask comprising the forehead support 10—shown in FIGS. 1 to 7—with the spring integrated into the forehead support stem.

FIG. 8 shows a vertical cross-section of a respiratory mask 11 comprising the forehead support 10—shown in FIGS. 1 to 7—with the spring 15 integrated into the forehead support stem 12. The forehead rest 13 with the guide bar 14 is additionally shown. The forehead rest 13 is thereby arranged at an angle to the guide bar 14. The angle between the guide bar 14 and the forehead rest 13 is between 1 and 30°, in particular between 5 and 15°. In FIG. 8, a cross-section through the structure of the spring 15 is additionally shown. It will be seen that the spring 15 comprises two folds which point toward the patient, wherein a fold remote from the patient is formed between the two folds. Such folding of the spring 15 contributes to better introduction of the forehead rest 13 with the guide bar 14 into the forehead support stem 12. The spring 15 additionally contributes toward vertical movability of the guide bar 14.

Figure 9:
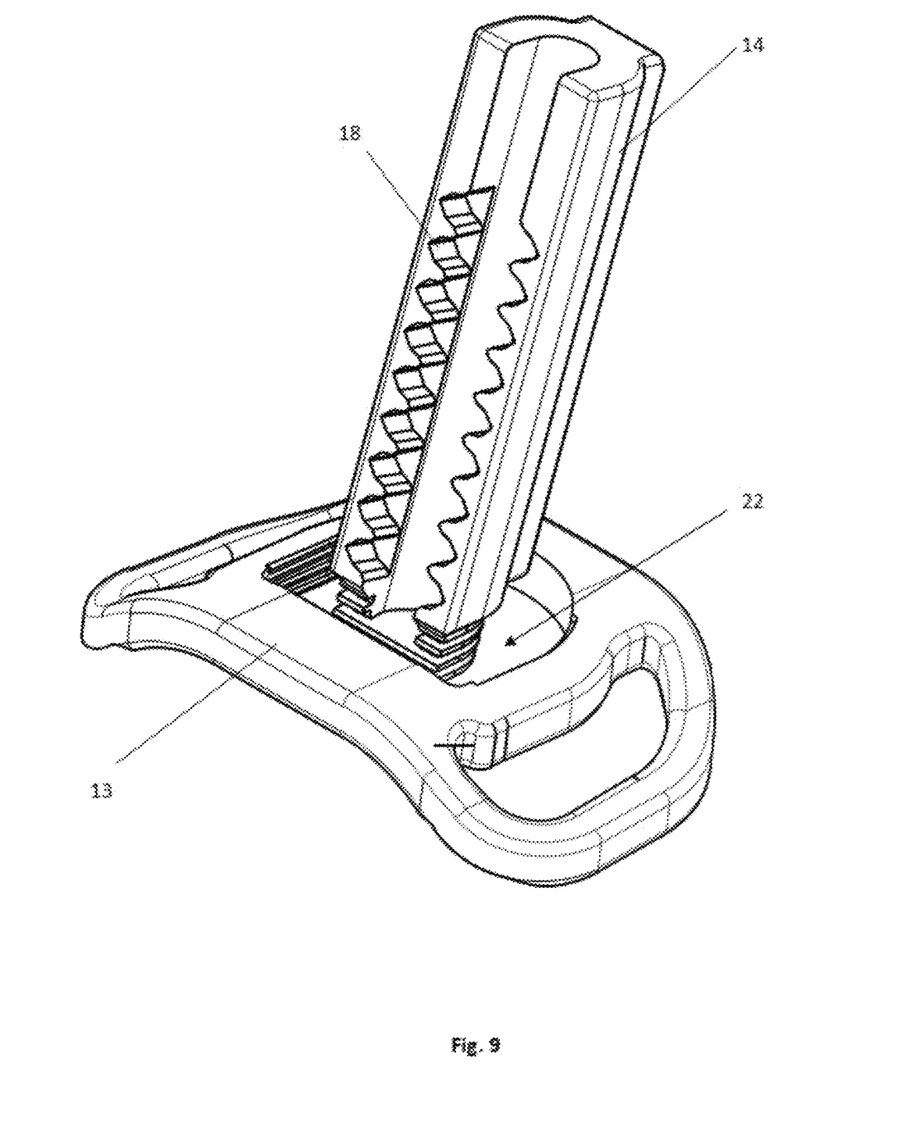
FIG. 9 is a perspective view of the embodiment of the forehead rest—shown in FIGS. 4 to 8—comprising the guide bar.

FIG. 9 shows a perspective view of the embodiment of the forehead rest 13—shown in FIGS. 4 to 8—comprising the guide bar 14. The forehead rest 13 is connected to the guide bar 14 via a contact region 22. The contact region 22 can be formed by an elastomer. In FIG. 9, the contact region 22 is shown empty. The contact region 22 is thereby in the form of a recess 26 in the forehead rest 13. Contact surfaces 25 are shown, which contact surfaces are adapted to receive an elastomer—not shown—for connecting the forehead rest 13 to the guide bar 14. The contact surfaces 25 are formed at an end of the guide bar 14 that is close to the patient and on at least two surfaces of the forehead rest 13, which form lateral surfaces of the recess 26 in the forehead rest 13.

Figure 10:
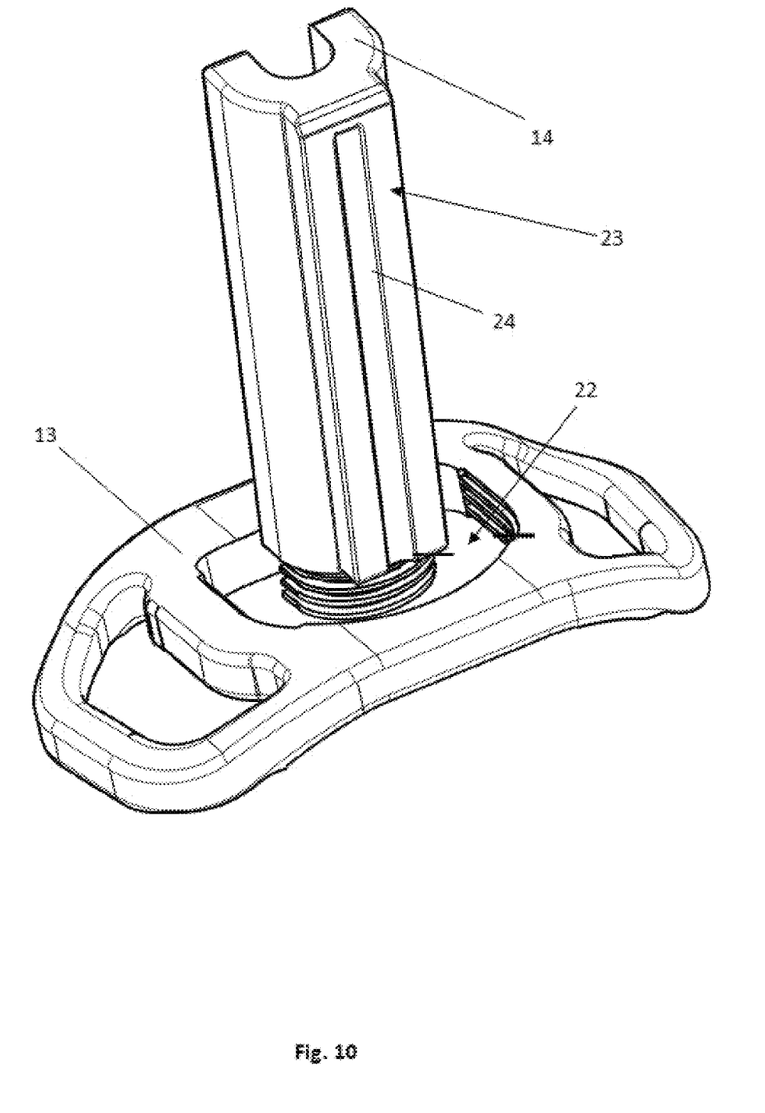
FIG. 10 is a further perspective view of the embodiment of the forehead rest—shown in FIGS. 4 to 9—comprising the guide bar.

FIG. 10 shows a further perspective view of the embodiment of the forehead rest 13—shown in FIGS. 4 to 8—comprising the guide bar 14. The underside of the guide bar 14, which comprises a running region 23 of the guide bar 14, is shown. A running surface 24 extends through the running region 23 along the longitudinal axis of the guide bar 14. In the present embodiment, the running surface is semicircular and closed on the side of the guide bar 14 that is remote from the patient. The running surface 24 receives the limiting projection 19, wherein the limiting projection 19 can be guided as far as the closed end of the running surface 24. By applying a pulling force, the limiting projection 19 can be pulled over the closed end of the running surface 24.

Figure 11:
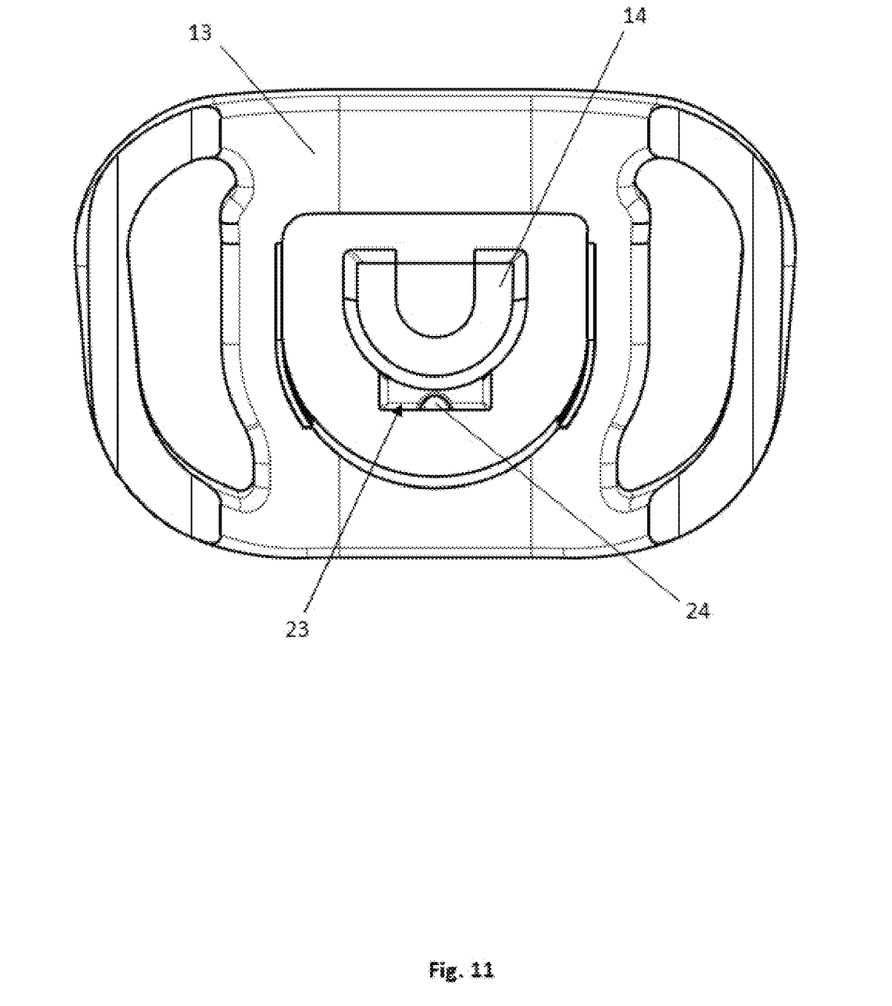
FIG. 11 is a detail view of the embodiment of the forehead rest—shown in FIGS. 4 to 10.

FIG. 11 shows a detail view of the embodiment of the forehead rest 13—shown in FIGS. 4 to 10. The running region 23 and the running surface 24 on the underside of the guide bar 14 are shown. The U-shaped form of the guide bar 14 is also shown.

Figure 12:
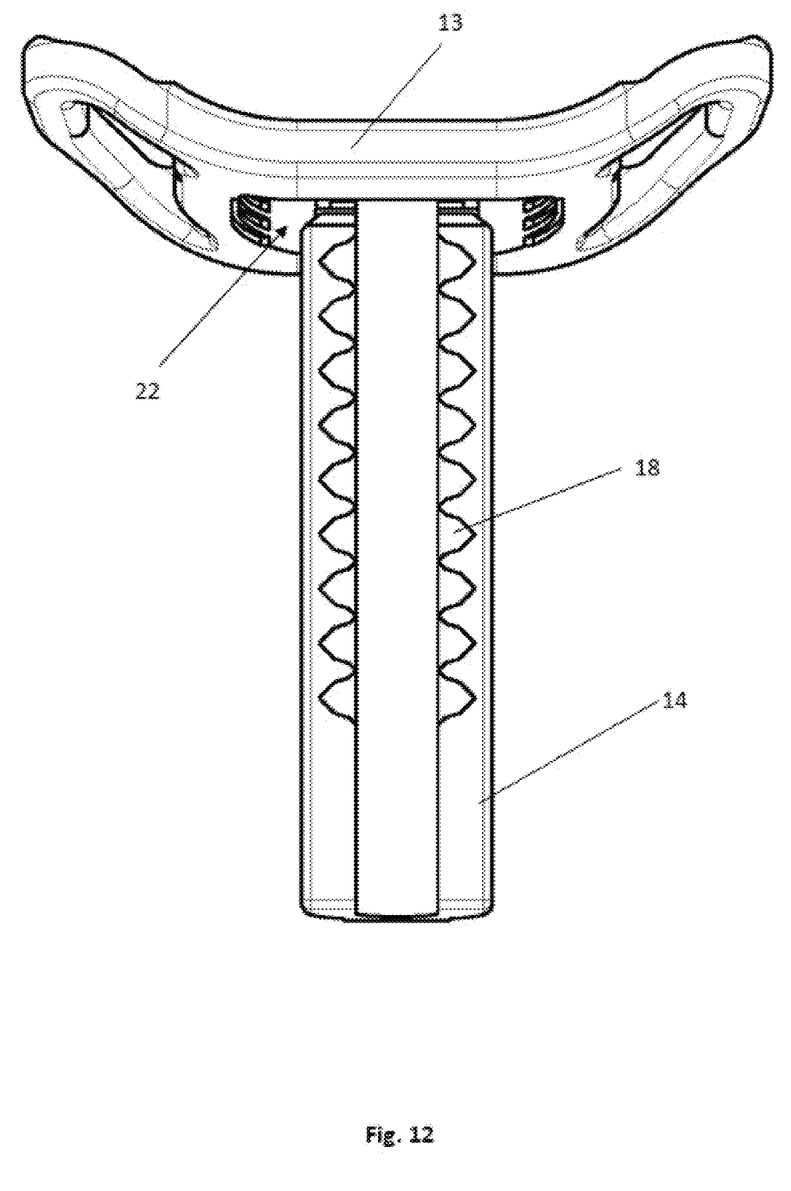
FIG. 12 is a detail view of the forehead rest—shown in FIGS. 4 to 11—comprising the guide bar.

FIG. 12 shows a detail view of the forehead rest 13—shown in FIGS. 4 to 11—comprising the guide bar 14. The guide bar 14 with the recesses 18 into which the locking pins 17a, 17b—shown in FIGS. 1 to 3—engage is shown. By pressing the first stem portion 12a and the second stem portion 12b together, a locking position of the locking pins 17a, 17b in the recesses 18 of the guide bar 14 can be adjusted.

LIST OF REFERENCE NUMERALS 10 forehead support
11 respiratory mask
12 forehead support stem
12a first stem portion
12b second stem portion
13 forehead rest 14 guide bar
15 resilient element, spring
16a, 16b guide projection
17a, 17b locking pin
18 recesses
19 limiting projection
bearing surface
21 retaining element
22 contact region
23 running region
24 running surface
25 contact surfaces
26 recess of the forehead rest

What is claimed is:

1. A forehead support for supporting a respiratory mask, wherein the forehead support comprises a stem and a forehead rest, the forehead rest comprising a single straight guide bar which is configured to be guided over a resilient element which is formed in the forehead support stem, and wherein
   (i) the forehead support stem is forked with a first stem portion and a second stem portion, the resilient element being formed between the first stem portion and the second stem portion.

2. The forehead support of claim 1, wherein the resilient element is in the form of a spring.

3. The forehead support of claim 1, wherein the first stem portion and/or the second stem portion comprises at least one locking pin.

4. The forehead support of claim 1, wherein the first stem portion and/or the second stem portion comprises at least one guide projection, at least one locking pin being formed on the at least one guide projection.

5. The forehead support of claim 1, wherein the guide bar lies on the resilient element, the resilient element supporting and limiting the guide bar.

6. The forehead support of claim 1, wherein the first stem portion and the second stem portion each comprise at least one bearing face for supporting the resilient element.

7. The forehead support of claim 1, wherein the first stem portion and the second stem portion are configured and formed as an operating element.

8. The forehead support of claim 1, wherein the resilient element comprises at least one limiting projection which is adapted to limit a guiding of the guide bar.

9. The forehead support of claim 1, wherein the guide bar comprises recesses.

10. The forehead support of claim 9, wherein the forehead support is forked and locking pins comprised in a first stem portion and/or a second stem portion of the forked forehead support stem are adapted to engage into the recesses of the guide bar, to delimit the guide bar laterally and to center the guide bar on the resilient element.

11. The forehead support of claim 1, wherein the forehead rest is movably connected to the guide bar.

12. The forehead support of claim 1, wherein the forehead rest is flexibly adjustable, a tilting movement of the forehead rest relative to the longitudinal axis of the guide bar being adjustable in an angle between 1° and 30°.

13. The forehead support of claim 1, wherein a connection between the forehead rest and the guide bar is formed by an element of a resilient material.

14. The forehead support of claim 1, wherein a connection between the forehead rest and the guide bar comprises a ball joint or a pivot joint.

15. The forehead support of claim 1, wherein the resilient element comprises a groove which is adapted to guide the resilient element in the guide bar.

16. A forehead support for supporting a respiratory mask, wherein the forehead support comprises a forehead support stem and a forehead rest, the forehead rest comprising a single straight guide bar, and the forehead support stem being forked with a first stem portion and a second stem portion and a resilient element in the form of a spring formed between the first and second stem portions.

* * * * *